(12) United States Patent
Tsuchimoto

(10) Patent No.: US 12,016,658 B2
(45) Date of Patent: Jun. 25, 2024

(54) CORE BODY THERMOMETER

(71) Applicant: Murata Manufacturing Co., Ltd., Nagaokakyo (JP)

(72) Inventor: Hirofumi Tsuchimoto, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 628 days.

(21) Appl. No.: 17/329,208

(22) Filed: May 25, 2021

(65) Prior Publication Data

US 2021/0275032 A1   Sep. 9, 2021

Related U.S. Application Data

(60) Division of application No. 15/811,720, filed on Nov. 14, 2017, now Pat. No. 11,045,091, which is a continuation of application No. PCT/JP2016/063553, filed on May 2, 2016.

(30) Foreign Application Priority Data

May 15, 2015   (JP) .................................. 2015-100039

(51) Int. Cl.
*A61B 5/01* (2006.01)
*G01K 1/16* (2006.01)
*G01K 7/00* (2006.01)
*G01K 13/20* (2021.01)

(52) U.S. Cl.
CPC .................. *A61B 5/01* (2013.01); *G01K 1/16* (2013.01); *G01K 1/165* (2013.01); *G01K 7/00* (2013.01); *G01K 13/20* (2021.01)

(58) Field of Classification Search
CPC .......... A61B 5/01; A61B 5/6833; G01K 1/16; G01K 1/165; G01K 7/00; G01K 13/20
See application file for complete search history.

(56) References Cited

PUBLICATIONS

Tsuchimoto, "Core Body Thermometer", U.S. Appl. No. 15/811,720, filed Nov. 14, 2017.

*Primary Examiner* — Sean P Dougherty
(74) *Attorney, Agent, or Firm* — Keating & Bennett, LLP

(57) ABSTRACT

A core body thermometer includes a substrate, a heat receiving terminal with which heat from a subject is received and which divides the heat into first heat flow and second heat flow and causes the first heat flow and the second heat flow to flow out, a first heat flow measurement system that measures the first heat flow using a first input-side temperature sensor and a first output-side temperature sensor, a second heat flow measurement system that measures the second heat flow using a second input-side temperature sensor and a second output-side temperature sensor, a first thermal resistance body provided between the heat receiving terminal and the first input-side temperature sensor, and a second thermal resistance body provided between the heat receiving terminal and the second input-side temperature sensor.

13 Claims, 10 Drawing Sheets

CORE BODY THERMOMETER

CROSS REFERENCE TO RELATED APPLICATIONS

This application claims the benefit of priority to Japanese Patent Application No. 2015-100039 filed on May 15, 2015 and is a Continuation Application of PCT Application No. PCT/JP2016/063553 filed on May 2, 2016. The entire contents of each application are hereby incorporated herein by reference.

BACKGROUND OF THE INVENTION

1. Field of the Invention

The present invention relates to a core body thermometer that measures the core body temperature of a subject.

2. Description of the Related Art

Non-heating-type thermometers including two pairs of heat flow detection structures are generally known as thermometers that measures the core body temperatures of subjects (for example, refer to Japanese Unexamined Patent Application Publication No. 2013-200152). The two pairs of heat flow detection structures are each composed of a certain thermal resistance, a first temperature sensor, and a second temperature sensor. The thermal resistance is sandwiched between the first temperature sensor and the second temperature sensor. In contrast, heating-type thermometers using heating elements (heaters) are also known as thermometers that measure the core body temperatures of subjects (for example, refer to Japanese Examined Patent Application Publication No. S56-4848).

The non-heating-type thermometer described in Japanese Unexamined Patent Application Publication No. 2013-200152 detects the difference between the temperatures detected by the first and second temperature sensors with the respective high-frequency detection structures to calculate the heat flow from deep portions of a subject, so as to calculate the core body temperature. However, since the two temperature sensors that are in contact with the body surface of the subject are provided in this configuration, the heat is input into the thermometer at two nodes. Accordingly, the thermal resistance in the subject is varied depending on the location because the tissue of the subject and the shape of the tissue are varied depending on the location. There is a problem in that the variation in the thermal resistance in the subject results in uncertain factors in the measurement of the body temperature to degrade the accuracy in the calculation of the core body temperature.

The heating-type thermometer described in Japanese Examined Patent Application Publication No. S56-4848 has a configuration in which the first and second temperature sensors are arranged so as to sandwich the heat insulating body therebetween and the heating element is arranged on the second temperature sensor with the heat insulating body sandwiched between the heating element and the second temperature sensor. In the heating-type thermometer, the difference in temperature between the first temperature sensor and the second temperature sensor is made equal to zero by controlling the heating element so that the temperature of the first temperature sensor at the subject side is balanced with the temperature of the second temperature sensor at the heating element side to calculate the core body temperature. However, since the heating element is provided in this configuration, there is a problem in that current consumption is increased. In addition, the manufacturing cost may possibly be increased due to a control circuit for the heating element.

SUMMARY OF THE INVENTION

Preferred embodiments of the present invention provide core body thermometers that include no heat source for heat generation and that estimate the core body temperature by receiving the heat from a subject at one node.

A preferred embodiment of the present invention includes a core body thermometer that estimates a core body temperature of a subject based on a first heat flow and a second heat flow flowing from the subject. The core body thermometer includes a substrate; a heat receiving terminal which is provided on the substrate, with which heat from the subject is received, and which divides the heat into the first heat flow and the second heat flow and causes the first heat flow and the second heat flow to flow out; a first heat flow measurement system that measures the first heat flow using a first input-side temperature sensor located at an upstream side of the first heat flow and a first output-side temperature sensor located at a downstream side of the first heat flow; a second heat flow measurement system that measures the second heat flow using a second input-side temperature sensor located at an upstream side of the second heat flow and a second output-side temperature sensor located at a downstream side of the second heat flow; a first thermal resistance body that is provided between the heat receiving terminal and the first input-side temperature sensor and that has a predetermined thermal resistance value; and a second thermal resistance body that is provided between the heat receiving terminal and the second input-side temperature sensor and that has a predetermined thermal resistance value.

In a core body thermometer according to a preferred embodiment of the present invention, the first thermal resistance body is provided as a first thermal resistance layer laminated between the heat receiving terminal and the first input-side temperature sensor, and the second thermal resistance body is provided as a second thermal resistance layer laminated between the heat receiving terminal and the second input-side temperature sensor.

In a core body thermometer according to a preferred embodiment of the present invention, the first thermal resistance body is provided as a first thermal resistance component, and the second thermal resistance body is provided as a second thermal resistance component.

A core body thermometer according to a preferred embodiment of the present invention includes one pair of thermal conductive plates that sandwich the substrate with the heat receiving terminal and multiple vias that pass through the substrate and that connect the heat receiving terminal to the one pair of thermal conductive plates. The first thermal resistance body is provided between one of the thermal conductive plates and the first input-side temperature sensor, and the second thermal resistance body is provided between the other of the thermal conductive plates and the second input-side temperature sensor.

A core body thermometer according to a preferred embodiment of the present invention estimates a core body temperature of a subject based on first heat flow and second heat flow flowing from the subject. The core body thermometer includes a substrate having a predetermined thermal resistance value; a heat receiving terminal that is provided on one surface of the substrate and that divides heat received from the substrate into the first heat flow and the second heat flow and causes the first heat flow and the second heat flow to flow out; a first heat flow measurement system that is provided on the other surface of the substrate and that measures the first heat flow using a first input-side temperature sensor located at an upstream side of the first heat flow and a first output-side temperature sensor located at a downstream side of the first heat flow; and a second heat flow measurement system that is provided on the other surface of the substrate and that measures the second heat flow using a second input-side temperature sensor located at an upstream side of the second heat flow and a second output-side temperature sensor located at a downstream side of the second heat flow.

A core body thermometer according to a preferred embodiment of the present invention includes a first input-side heat insulating body provided between the first input-side temperature sensor and the first output-side temperature sensor so as to cover the first input-side temperature sensor and a second input-side heat insulating body placed between the second input-side temperature sensor and the second output-side temperature sensor so as to cover the second input-side temperature sensor.

A core body thermometer according to a preferred embodiment of the present invention further includes a first output-side heat insulating body that covers the first output-side temperature sensor and/or a second output-side heat insulating body that covers the second output-side temperature sensor.

A core body thermometer according to a preferred embodiment of the present invention further includes a charging circuit that charges the core body thermometer with electric power that is externally supplied in a wireless manner and a transmission circuit that externally transmits the core body temperature of the subject, which is estimated with the first heat flow measurement system and the second heat flow measurement system.

According to a preferred embodiment of the present invention, a configuration is provided in which the heat of the subject, input into the core body thermometer with the heat receiving terminal, is divided into the first heat flow and the second heat flow and the core body temperature of the subject is estimated based on the first heat flow and the second heat flow. Since the heat from the subject is input into the core body thermometer at one node, that is, the single heat receiving terminal, one heat flow occurs from deep portions of the subject to the portion where the heat is input into the core body thermometer. As a result, even when the thermal resistance in the subject is varied with the location due to the tissue of the subject and the shape of the tissue, the heat from the subject is capable of being input into the core body thermometer without being affected by the variation in the thermal resistance in the subject depending on the location. Accordingly, uncertain factors in the measurement of the core body temperature are reduced to increase the accuracy in the measurement of the core body temperature of the subject.

In addition, according to a preferred embodiment of the present invention, the first thermal resistance body is provided between the heat receiving terminal and the first input-side temperature sensor and the second thermal resistance body is provided between the heat receiving terminal and the second input-side temperature sensor. With this configuration, since the thermal resistance value between the first heat flow measurement system and the second heat flow measurement system is high, it is possible to reduce or prevent the heat flow flowing from the first heat flow measurement system to the second heat flow measurement system (or from the second heat flow measurement system to the first heat flow measurement system). As a result, the first heat flow measurement system and the second heat flow measurement system are capable of independently measuring the heat flow input from deep portions of the subject without being affected by the heat flow flowing through the other heat flow measurement system. Accordingly, it is possible to increase the accuracy in the measurement of the core body temperature of the subject, compared to a configuration in which the first thermal resistance body and the second thermal resistance body are removed.

Furthermore, according to a preferred embodiment of the present invention, a configuration is provided in which the core body temperature of the subject is estimated based on the first heat flow and the second heat flow, which flow from the subject, without using any heating element. With this configuration, since it is not necessary to use the heat source for heat generation, the power consumption is reduced. In addition, since it is not necessary to use a control circuit for the heating element, the manufacturing cost of the core body thermometer is reduced.

According to a preferred embodiment of the present invention, the first thermal resistance body is laminated between the heat receiving terminal and the first input-side temperature sensor and the second thermal resistance body is laminated between the heat receiving terminal and the second input-side temperature sensor. With this configuration, for example, adjusting the thickness dimensions or the materials of the respective thermal resistance layers enables the thermal resistance value between the first heat flow measurement system and the second heat flow measurement system to be easily increased. As a result, it is possible to reduce or prevent the heat flow flowing between the first heat flow measurement system and the second heat flow measurement system to increase the accuracy in the measurement of the core body temperature of the subject.

According to a preferred embodiment of the present invention, the first and second thermal resistance bodies are provided as the first and second thermal resistance components. Accordingly, since the profiles of the first and second thermal resistance bodies are low, compared to the core body thermometer in which the first and second thermal resistance bodies are laminated, it is possible to reduce the size of the entire core body thermometer.

According to a preferred embodiment of the present invention, it is possible to divide the heat (heat flow) received from the subject into the first heat flow and the second heat flow with the multiple vias and one pair of thermal conductive plates and to supply the first heat flow and the second heat flow to the first heat flow measurement system and the second heat flow measurement system, respectively. In addition, since the thermal resistance values of the first thermal resistance body and the second thermal resistance body are difficult to vary (are less affected), for example, if the substrate is deformed (for example, folded), it is possible to reliably and accurately measure the core body temperature even if the substrate is deformed.

According to a preferred embodiment of the present invention, the substrate has the predetermined thermal resistance value and the substrate is capable of being used as the first thermal resistance body and the second thermal resistance body described above. In other words, the substrate also has the functions of the first thermal resistance body and the second thermal resistance body. Accordingly, it is possible to further simplify the structure of the core body thermometer in order to reduce the size and weight (make the profile low) and to reduce the cost.

According to a preferred embodiment of the present invention, it is possible to prevent the influence of the air flow to the first input-side temperature sensor and the second input-side temperature sensor and to make the first input-side temperature sensor and the second input-side temperature sensor less affected by the fluctuation of the outside air temperature. Accordingly, it is possible to reduce or prevent noise in the outputs from the first input-side temperature sensor and the second input-side temperature sensor.

According to a preferred embodiment of the present invention, it is possible to prevent the influence of the air flow to the first output-side temperature sensor and the second output-side temperature sensor and to make the first output-side temperature sensor and the second output-side temperature sensor less affected by the fluctuation of the outside air temperature. Accordingly, it is possible to reduce or prevent noise in the outputs from the first output-side temperature sensor and the second output-side temperature sensor.

According to a preferred embodiment of the present invention, the core body thermometer has a configuration in which the core body thermometer is capable of being externally charged in a wireless manner and the core body temperature of the subject is capable of being externally transmitted. Accordingly, since the core body thermometer is capable of being used with no cable and the wiring is not used in the measurement of the core body temperature, it is possible to improve non-invasiveness.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Core body thermometers according to preferred embodiments of the present invention will be described in detail with reference to the drawings.

Figure 1:
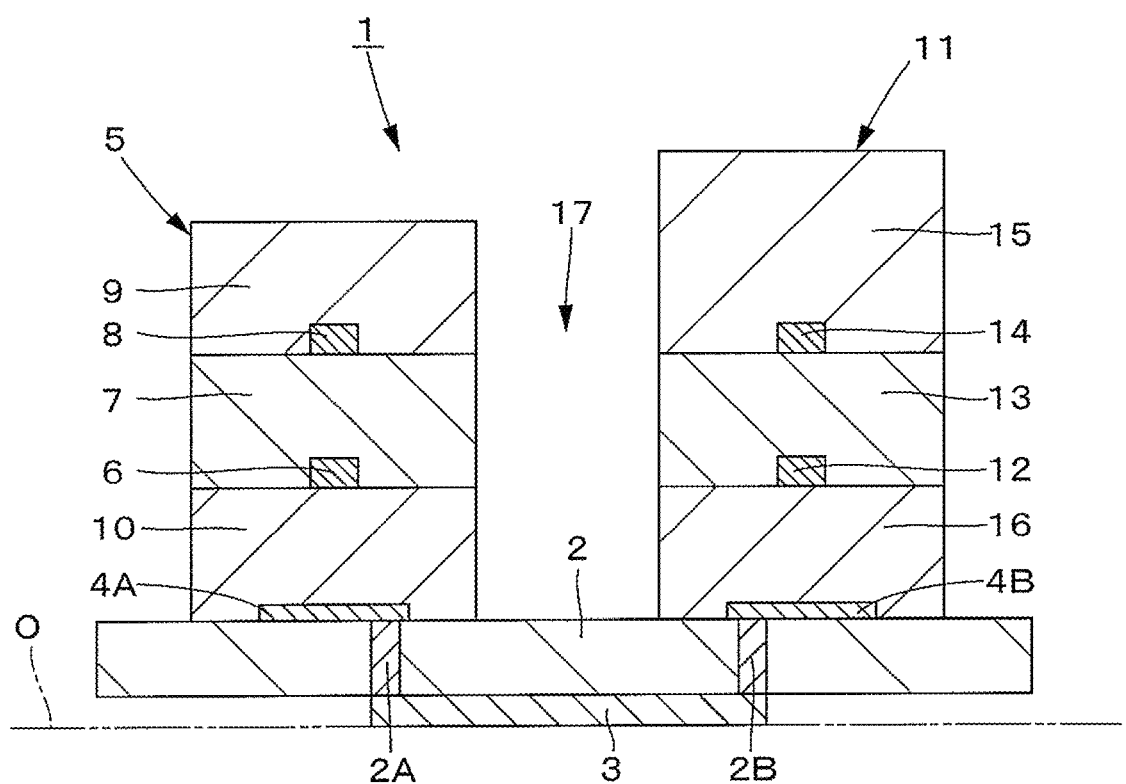
FIG. 1 is a cross-sectional view illustrating the configuration of a core body thermometer according to a first preferred embodiment of the present invention.
Figure 2:
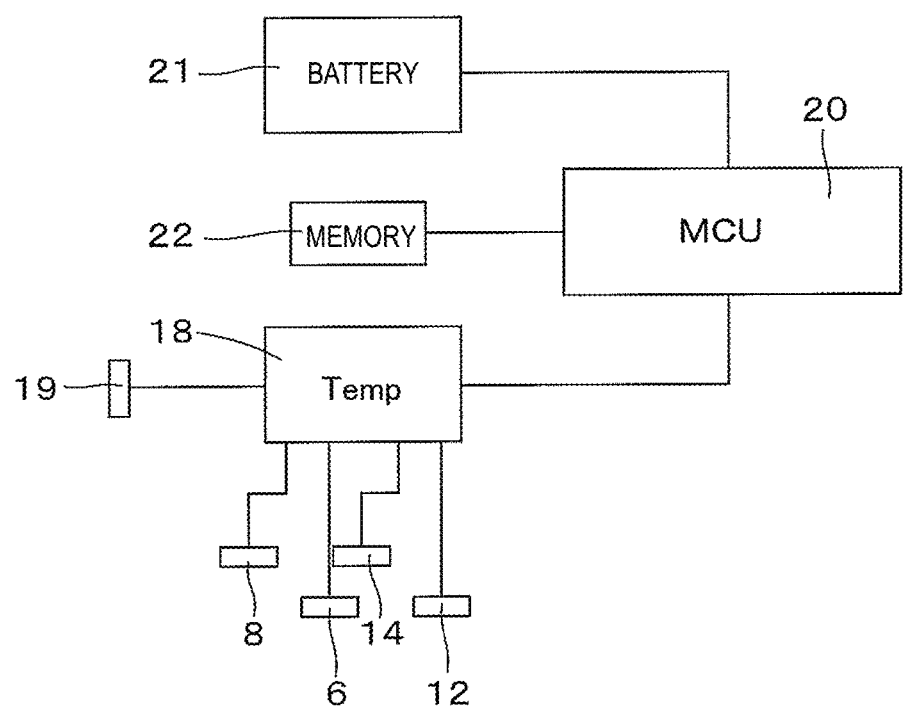
FIG. 2 is a block diagram illustrating the internal configuration of the core body thermometer according to the first preferred embodiment of the present invention.
Figure 3:
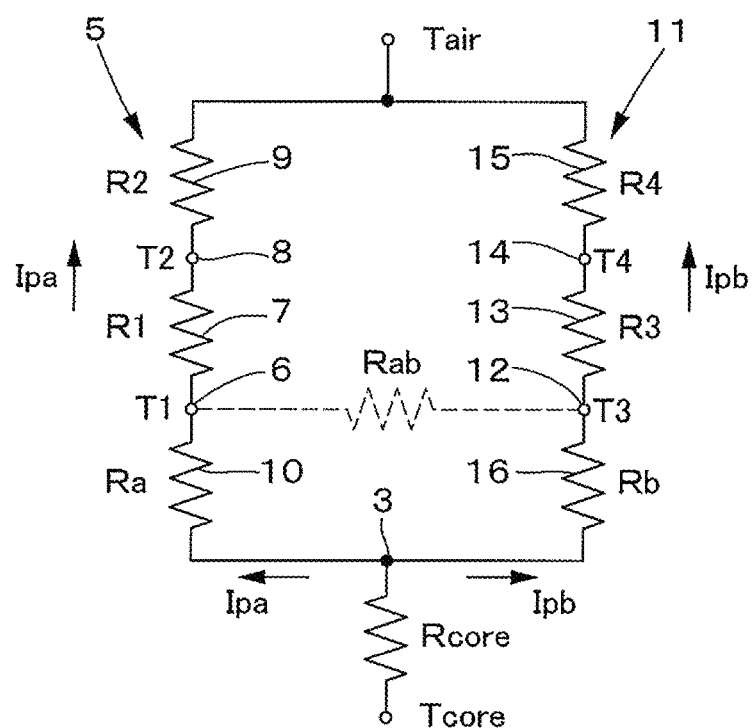
FIG. 3 is an equivalent circuit diagram illustrating heat flow in the core body thermometer according to the first preferred embodiment of the present invention.

FIG. 1 to FIG. 3 illustrate a first preferred embodiment of the present invention. A core body thermometer 1 includes a substrate 2 heat receiving terminal 3, a first heat flow measurement system 5, a second heat flow measurement system 11, a first thermal resistance body 10, and a second thermal resistance body 16. The core body thermometer 1 estimates a core body temperature Tcore of a subject O based on first heat flow Ipa and second heat flow Ipb flowing from the subject O.

The substrate 2 preferably has a flat plate shape and is made of an insulating material, such as polyimide, which has a thermal conductivity lower than that of the subject O. The substrate 2 may be, for example, a deformable flexible substrate or an undeformable printed circuit board. The rear surface (bottom surface) of the substrate 2 is an opposing surface opposed to the subject O. Accordingly, the heat receiving terminal 3 described below is provided on the rear surface of the substrate 2. The front surface (upper surface) of the substrate 2 is a mounting surface on which thermal conductive plates 4A and 4B, a temperature measurement circuit 18, an arithmetic processing circuit 20, a battery 21, a memory 22, and other components, which are described below, are mounted.

Vias 2A and 2B passing through the substrate 2 in the thickness direction are provided in the substrate 2. The vias 2A and 2B preferably are formed by forming through holes passing through the substrate 2 using laser beam machining or other suitable methods and, for example, plating the through holes with metal conductor. The vias 2A and 2B have thermal conductivity. The heat receiving terminal 3 is connected to the thermal conductive plate 4A through the via 2A and is connected to the thermal conductive plate 4B through the via 2B. A case is exemplified in FIG. 1 in which one via 2A and one via 2B are provided in the substrate 2. However, a case in which one via 2A and one via 2B are provided is not necessarily provided, and multiple vias 2A and multiple vias 2B may be provided in consideration of the thermal conductivity between the heat receiving terminal 3 and the thermal conductive plates 4A and 4B.

The heat receiving terminal 3 is positioned on the lower surface of the substrate 2. The heat receiving terminal 3 preferably has a flat plate shape or a film shape and is made of a material having a thermal conductivity higher than that of the subject O, for example, a metallic material, such as aluminum. The heat receiving terminal 3 is in contact with the body surface of the subject O and heat from the subject O is input into the core body thermometer 1 with the heat receiving terminal 3. The heat receiving terminal 3 divides the heat from the subject O into the first heat flow Ipa and the second heat flow Ipb and causes the first heat flow Ipa and the second heat flow Ipb to flow into the vias 2A and 2B.

The thermal conductive plate 4A is positioned on the lower surface of the first thermal resistance body 10 and is provided on the front surface of the substrate 2. The thermal conductive plate 4B is positioned on the lower surface of the second thermal resistance body 16 and is provided on the front surface of the substrate 2. These thermal conductive plates 4A and 4B each preferably have a flat plate shape or a film shape and are made of a material, such as aluminum, for example, having a high thermal conductivity, similar to the heat receiving terminal 3. The thermal conductive plate 4A is connected to the via 2A and the thermal conductive plate 4B is connected to the via 2B. The thermal conductive plate 4A conducts the heat of the subject O, which is input into the core body thermometer 1 through the heat receiving terminal 3, to the first heat flow measurement system 5 as the first heat flow Ipa. The thermal conductive plate 4B conducts the heat of the subject O, which is input into the core body thermometer 1 through the heat receiving terminal 3, to the second heat flow measurement system 11 as the second heat flow Ipb.

The first heat flow measurement system 5 is positioned on the upper surface side of the thermal conductive plate 4A. The first heat flow measurement system 5 includes a first input-side temperature sensor 6, a first input-side heat insulating body 7, a first output-side temperature sensor 8, and a first output-side heat insulating body 9. In the first heat flow measurement system 5, the first input-side temperature sensor 6 and the first output-side temperature sensor 8 are located at different positions on a path along which the first heat flow Ipa flows. With the above configuration, the first heat flow measurement system 5 measures the first heat flow Ipa flowing from the thermal conductive plate 4A to the upper side of the first heat flow measurement system 5 based on temperatures T1 and T2 measured by the first input-side temperature sensor 6 and the first output-side temperature sensor 8, respectively.

The first input-side temperature sensor 6 is positioned above the thermal conductive plate 4A (i.e., immediately above the thermal conductive plate 4A) in the thickness direction of the substrate 2 and is provided on the first thermal resistance body 10. In other words, the first input-side temperature sensor 6 is located at the upstream side of the first heat flow Ipa. The first input-side temperature sensor 6 is preferably, for example, a thermistor, and measures the temperature T1 at the upstream side of the first heat flow Ipa.

The first input-side heat insulating body 7 is positioned on the first thermal resistance body 10 to cover the first input-side temperature sensor 6. The first input-side heat insulating body 7 preferably has a sheet shape and is made of a material, such as urethane, for example, having a low thermal conductivity. The first input-side temperature sensor 6 is sandwiched between the first input-side heat insulating body 7 and the first thermal resistance body 10. Accordingly, the first input-side temperature sensor 6 is blocked from the outside air with the first input-side heat insulating body 7 and the first thermal resistance body 10.

The first input-side heat insulating body 7 is sandwiched between the first input-side temperature sensor 6 and the first output-side temperature sensor 8. The first input-side heat insulating body 7 has a predetermined thickness dimension. Accordingly, the first input-side heat insulating body 7 has a predetermined thermal resistance value R1 between the first input-side temperature sensor 6 and the first output-side temperature sensor 8 depending on the thickness dimension.

The first output-side temperature sensor 8 is positioned above the thermal conductive plate 4A (i.e., immediately above the thermal conductive plate 4A) in the thickness direction of the substrate 2 and is provided on the first input-side heat insulating body 7. In other words, the first output-side temperature sensor 8 is located at the downstream side of the first heat flow Ipa. The first output-side temperature sensor 8 is preferably, for example, a thermistor, and measures the temperature T2 at the downstream side of the first heat flow Ipa.

The first output-side heat insulating body 9 is positioned on the first input-side heat insulating body 7 to cover the first output-side temperature sensor 8. The first output-side heat insulating body 9 preferably has a sheet shape and is made of a material, such as urethane, for example, having a low thermal conductivity. The first output-side temperature sensor 8 is sandwiched between the first output-side heat insulating body 9 and the first input-side heat insulating body 7. Accordingly, the first output-side temperature sensor 8 is blocked from the outside air with the first output-side heat insulating body 9 and the first input-side heat insulating body 7. In this case, in order to reduce or prevent the influence of thermal contact resistance, for example, the first output-side heat insulating body 9 and the first input-side heat insulating body 7 preferably have the same or substantially the same thermal conductivity. Accordingly, the first output-side heat insulating body 9 is preferably made of the same material as that of the first input-side heat insulating body 7. The first output-side heat insulating body 9 is sandwiched between the first output-side temperature sensor 8 and the outside air. The first output-side heat insulating body 9 has a predetermined thickness dimension. Accordingly, the first output-side heat insulating body 9 has a predetermined thermal resistance value R2 between the first output-side temperature sensor 8 and the outside air depending on the thickness dimension.

The first thermal resistance body 10 is a first thermal resistance layer laminated between the heat receiving terminal 3 and the first input-side temperature sensor 6. Specifically, the first thermal resistance body 10 is provided between the substrate 2 and the first input-side heat insulating body 7 and is located between the thermal conductive plate 4A, which is connected to the heat receiving terminal 3 with the thermal conductivity, and the first input-side temperature sensor 6. The first thermal resistance body 10 preferably has a sheet shape and is made of a material, such as urethane, for example, having a low thermal conductivity. The first thermal resistance body 10 is provided on the upper surface side of the substrate 2 so as to cover the thermal conductive plate 4A.

The first thermal resistance body 10 is sandwiched between the thermal conductive plate 4A and the first input-side temperature sensor 6. The first thermal resistance body 10 has a predetermined thickness dimension. Accordingly, the first thermal resistance body 10 has a predetermined thermal resistance value Ra between the thermal conductive plate 4A and the first input-side temperature sensor 6 depending on the thickness dimension.

The thermal resistance value Ra of the first thermal resistance body 10 is set in consideration of thermal isolation between the first heat flow measurement system 5 and the second heat flow measurement system 11. Accordingly, the first thermal resistance body 10 prevents the heat flow from flowing between the first heat flow measurement system 5 and the second heat flow measurement system 11 with the second thermal resistance body 16. In this case, in order to reduce or prevent the influence of the thermal contact resistance, for example, the first thermal resistance body 10 and the first input-side heat insulating body 7 preferably have the same or substantially the same thermal conductivity. Accordingly, the first thermal resistance body 10 is preferably made of the same material as those of the first input-side heat insulating body 7 and the first output-side heat insulating body 9.

The second heat flow measurement system 11 is positioned on the upper surface side of the thermal conductive plate 4B. The second heat flow measurement system 11 includes a second input-side temperature sensor 12, a second input-side heat insulating body 13, a second output-side temperature sensor 14, and a second output-side heat insulating body 15. In the second heat flow measurement system 11, the second input-side temperature sensor 12, and the second output-side temperature sensor 14 are located at different positions along a path on which the second heat flow Ipb flows. With the above configuration, the second heat flow measurement system 11 measures the second heat flow Ipb flowing from the thermal conductive plate 4B to the upper side of the second heat flow measurement system 11 based on temperatures T3 and T4 measured by the second input-side temperature sensor 12 and the second output-side temperature sensor 14, respectively.

The second input-side temperature sensor 12 is positioned above the thermal conductive plate 4B (i.e., immediately above the thermal conductive plate 4B) in the thickness direction of the substrate 2 and is provided on the second thermal resistance body 16. In other words, the second input-side temperature sensor 12 is located at the upstream side of the second heat flow Ipb. The second input-side temperature sensor 12 is preferably, for example, a thermistor, and measures the temperature T3 at the upstream side of the second heat flow Ipb.

The second input-side heat insulating body 13 is positioned on the second thermal resistance body 16 to cover the second input-side temperature sensor 12. The second input-side heat insulating body 13 preferably has a sheet shape and is made of a material, such as urethane, for example, having a low thermal conductivity. The second input-side temperature sensor 12 is sandwiched between the second input-side heat insulating body 13 and the second thermal resistance body 16. Accordingly, the second input-side temperature sensor 12 is blocked from the outside air with the second input-side heat insulating body 13 and the second thermal resistance body 16.

The second input-side heat insulating body 13 is sandwiched between the second input-side temperature sensor 12 and the second output-side temperature sensor 14. The second input-side heat insulating body 13 has a predetermined thickness dimension. Accordingly, the second input-side heat insulating body 13 has a predetermined thermal resistance value R3 between the second input-side temperature sensor 12 and the second output-side temperature sensor 14 depending on the thickness dimension.

The second output-side temperature sensor 14 is positioned above the thermal conductive plate 4B (i.e., immediately above the thermal conductive plate 4B) in the thickness direction of the substrate 2 and is provided on the second input-side heat insulating body 13. In other words, the second output-side temperature sensor 14 is located at the downstream side of the second heat flow Ipb. The second output-side temperature sensor 14 is preferably, for example, a thermistor, and measures the temperature T4 at the downstream side of the second heat flow Ipb.

The second output-side heat insulating body 15 is positioned on the second input-side heat insulating body 13 to cover the second output-side temperature sensor 14. The second output-side heat insulating body 15 preferably has a sheet shape and is made of a material, such as urethane, for example, having a low thermal conductivity. The second output-side temperature sensor 14 is sandwiched between the second output-side heat insulating body 15 and the second input-side heat insulating body 13. Accordingly, the second output-side temperature sensor 14 is blocked from the outside air with the second output-side heat insulating body 15 and the second input-side heat insulating body 13.

The second output-side heat insulating body 15 is sandwiched between the second output-side temperature sensor 14 and the outside air. The second output-side heat insulating body 15 has a predetermined thickness dimension. Accordingly, the second output-side heat insulating body 15 has a predetermined thermal resistance value R4 between the second output-side temperature sensor 14 and the outside air depending on the thickness dimension.

In this case, the second output-side heat insulating body 15 preferably has a thickness dimension greater than that of the first output-side heat insulating body 9 in order to differentiate the heat flow value of the first heat flow Ipa from the heat flow value of the second heat flow Ipb. Accordingly, the thermal resistance value R4 of the second output-side heat insulating body 15 is higher than the thermal resistance value R2 of the first output-side heat insulating body 9. In order to reduce or prevent the influence of the thermal contact resistance, for example, the second output-side heat insulating body 15 and the second input-side heat insulating body 13 preferably have the same or substantially the same thermal conductivity. Accordingly, the second output-side heat insulating body 15 is preferably made of the same material as that of the second input-side heat insulating body 13.

The second thermal resistance body 16 is a second thermal resistance layer laminated between the heat receiving terminal 3 and the second input-side temperature sensor 12. Specifically, the second thermal resistance body 16 is provided between the substrate 2 and the second input-side heat insulating body 13 and is located between the thermal conductive plate 4B, which is connected to the heat receiving terminal 3 with the thermal conductivity, and the second input-side temperature sensor 12. The second thermal resistance body 16 preferably has a sheet shape and is made of a material, such as urethane, for example, having a low thermal conductivity. The second thermal resistance body 16 is provided on the upper side of the substrate 2 so as to cover the thermal conductive plate 4B.

The second thermal resistance body 16 is sandwiched between the thermal conductive plate 4B and the second input-side temperature sensor 12. The second thermal resistance body 16 has a predetermined thickness dimension. Accordingly, the second thermal resistance body 16 has a predetermined thermal resistance value Rb between the thermal conductive plate 4B and the second input-side temperature sensor 12 depending on the thickness dimension.

The thermal resistance value Rb of the second thermal resistance body 16 is set in consideration of the thermal isolation between the first heat flow measurement system 5 and the second heat flow measurement system 11. Accordingly, the second thermal resistance body 16 prevents the heat flow from flowing between the first heat flow measurement system 5 and the second heat flow measurement system 11 with the first thermal resistance body 10. In this case, in order to reduce or prevent the influence of the thermal contact resistance, for example, the second thermal resistance body 16 and the second input-side heat insulating body 13 preferably have the same or substantially the same thermal conductivity. Accordingly, the second thermal resistance body 16 is preferably made of the same material as those of the second input-side heat insulating body 13 and the second output-side heat insulating body 15.

The sum (Ra+Rb) of the thermal resistances of the first thermal resistance body 10 and the second thermal resistance body 16 is preferably set to a value at which the thermal resistance between the first input-side temperature sensor 6 and the second input-side temperature sensor 12 is higher than that, for example, in a case in which the first input-side temperature sensor 6 and the second input-side temperature sensor 12 are directly in contact with the body surface of the subject O. As illustrated in FIG. 3, when the first input-side temperature sensor 6 and the second input-side temperature sensor 12 are directly in contact with the body surface of the subject O, a thermal resistance value Rab between the first input-side temperature sensor 6 and the second input-side temperature sensor 12 is determined by the distance between the first input-side temperature sensor 6 and the second input-side temperature sensor 12 and the thermal conductivity near the body surface of the subject O. The sum (Ra+Rb) of the thermal resistances of the first thermal resistance body 10 and the second thermal resistance body 16 is preferably greater than the thermal resistance value Rab (Rab<Ra+Rb).

The sum (Ra+R1+R2) of the thermal resistances of the first thermal resistance body 10, the first input-side heat insulating body 7, and the first output-side heat insulating body 9 is preferably set so as to be different from the sum (Rb+R3+R4) of the thermal resistances of the second thermal resistance body 16, the second input-side heat insulating body 13, and the second output-side heat insulating body 15. As a result, the first heat flow Ipa has a value different from that of the second heat flow Ipb.

The first heat flow measurement system 5 is spaced away from the second heat flow measurement system 11. Similarly, the first thermal resistance body 10 is spaced away from the second thermal resistance body 16. Accordingly, a gap 17 is provided between the first heat flow measurement system 5 and the second heat flow measurement system 11. The gap 17 extends to a portion between the first thermal resistance body 10 and the second thermal resistance body 16. The gap 17 defines a heat insulating portion with which the first heat flow measurement system 5 is thermally isolated from the second heat flow measurement system 11 and thermally isolates the first thermal resistance body 10 from the second thermal resistance body 16.

As illustrated in FIG. 2, the temperature measurement circuit 18 defines a portion of a signal processing circuit that calculates the core body temperature Tcore of the subject O based on the temperatures T1 to T4 measured by the temperature sensors 6, 8, 12, and 14, respectively. The temperature measurement circuit 18 is provided on, for example, the substrate 2 and is connected to the respective temperature sensors 6, 8, 12, and 14. The temperature measurement circuit 18 is preferably defined by, for example, an amplifier and an analog-to-digital converter, which are not illustrated. The temperature measurement circuit 18 amplifies an analog signal supplied from each of the temperature sensors 6, 8, 12, and 14, converts the analog signal into a digital signal, and supplies the digital signal to the arithmetic processing circuit 20 described below. In addition to the temperature sensors 6, 8, 12, and 14, a temperature sensor 19 is also connected to the temperature measurement circuit 18. The temperature sensor 19 measures a temperature other than the temperature of the subject O (for example, outside air temperature).

The arithmetic processing circuit 20 defines a portion of the signal processing circuit, which calculates the core body temperature Tcore of the subject O. The arithmetic processing circuit 20 is preferably defined by, for example, a micro control unit (MCU) and calculates the core body temperature Tcore of the subject O based on the temperatures T1 to T4 of the respective temperature sensors 6, 8, 12, and 14, which are subjected to the signal processing in the temperature measurement circuit 18. Power is supplied from the battery 21 to the arithmetic processing circuit 20. The arithmetic processing circuit 20 stores the calculated core body temperature Tcore in the memory 22.

The core body thermometer 1 according to the present preferred embodiment is preferably configured as described above. A method of calculating the core body temperature Tcore of the subject O using the core body thermometer 1 will now be described.

First, when the heat receiving terminal 3 of the core body thermometer 1 is in contact with the body surface of the subject O, the equivalent circuit of the heat flow from deep portions of the subject O to the outside air is illustrated in FIG. 3. In this case, a thermal resistance value Rcore in the subject indicates the thermal resistance value of the subcutaneous tissue of the subject O.

Then, the arithmetic processing circuit 20 calculates the first and second heat flows Ipa and Ipb using the temperatures T1 to T4 measured by the temperature sensors 6, 8, 12, and 14, respectively. In this case, the first and second heat flows Ipa and Ipb are represented by Formula 1 and Formula 2, respectively:

$$Ipa = \frac{T1-T2}{R1} = \frac{Tcore-T1}{Rcore+Ra} \quad \text{Formula 1}$$

$$Ipb = \frac{T3-T4}{R3} = \frac{Tcore-T3}{Rcore+Rb} \quad \text{Formula 2}$$

Since the first and second thermal resistance bodies 10 and 16 have the known thermal resistance values Ra and Rb, respectively, the core body temperature Tcore of the subject O is able to be calculated by eliminating the thermal resistance value Rcore using Formula 1 and Formula 2 as a system of equations.

When the thermal resistance value Ra is equal to the thermal resistance value Rb, the core body temperature Tcore is able to be calculated using Formula 3 resulting from a modification of Formula 1 and Formula 2. In this case, a constant K is represented by Formula 4.

$$Tcore = \frac{(T3-T4) \times T1 - K(T1-T2) \times T3}{(T3-T4) - K(T1-T2)} \quad \text{Formula 3}$$

$$K = \frac{R3}{R1} \quad \text{Formula 4}$$

As described above, according to the first preferred embodiment, a configuration is provided in which the heat of the subject O, input into the core body thermometer 1 with the heat receiving terminal 3, is divided into the first heat flow Ipa and the second heat flow Ipb and the core body temperature Tcore of the subject O is calculated based on the first heat flow Ipa and the second heat flow Ipb. Since the heat from the subject O is input into the core body thermometer 1 at one node, that is, the single heat receiving terminal 3, one heat flow occurs from deep portions of the subject O to the heat receiving terminal 3. As a result, even when the thermal resistance in the subject is varied with the location due to the tissue of the subject and the shape of the tissue, the heat from the subject O is able to be input into the core body thermometer 1 without being affected by the variation in the thermal resistance in the subject depending on the location. Accordingly, uncertain factors in the measurement of the core body temperature are reduced to increase the accuracy in the measurement of the core body temperature Tcore of the subject O.

When the first input-side temperature sensor 6 and the second input-side temperature sensor 12 are directly in contact with the body surface of the subject O, the thermal resistance value Rab between the first input-side temperature sensor 6 and the second input-side temperature sensor 12 is determined by the thermal conductivity near the body surface of the subject O. According to the first preferred embodiment, the first thermal resistance body 10 is provided between the heat receiving terminal 3 and the first input-side temperature sensor 6 and the second thermal resistance body 16 is provided between the heat receiving terminal 3 and the second input-side temperature sensor 12. With this configuration, since the thermal resistance value (Ra+Rb) between the first heat flow measurement system 5 and the second heat flow measurement system 11 is higher than the thermal resistance value Rab caused by the subject O, it is possible to reduce or prevent the heat flow flowing between the first heat flow measurement system 5 and the second heat flow measurement system 11.

As a result, the first heat flow measurement system 5 and the second heat flow measurement system 11 are able to independently measure the heat flow input from deep portions of the subject O without being affected by the heat flow flowing through the other heat flow measurement system. Accordingly, it is possible to increase the accuracy in the measurement of the core body temperature Tcore of the subject O, compared to a configuration in which the first and second thermal resistance bodies 10 and 16 are removed. In addition, since the first heat flow measurement system 5 is able to be located near the second heat flow measurement system 11, it is possible to reduce the variation in the thermal resistance in the subject near the heat receiving terminal 3.

In addition, according to the first preferred embodiment, a configuration is provided in which the core body temperature Tcore of the subject O is calculated based on the first heat flow Ipa and the second heat flow Ipb, which flow from the subject O, without using any heating element. With this configuration, since it is not necessary to use the heat source for heat generation, the power consumption is reduced. In addition, since it is not necessary to use a control circuit for the heating element, the manufacturing cost of the core body thermometer 1 is reduced.

Furthermore, according to the first preferred embodiment, the first thermal resistance body 10 is laminated between the heat receiving terminal 3 and the first input-side temperature sensor 6 and the second thermal resistance body 16 is laminated between the heat receiving terminal 3 and the second input-side temperature sensor 12. With this configuration, for example, adjusting the thickness dimensions or the materials of the respective thermal resistance bodies 10 and 16 enables the thermal resistance value between the first heat flow measurement system 5 and the second heat flow measurement system 11 to be easily increased. As a result, it is possible to reduce or prevent the heat flow flowing between the first heat flow measurement system 5 and the second heat flow measurement system 11 to improve the thermal isolation between the first heat flow measurement system 5 and the second heat flow measurement system 11, so as to increase the accuracy in the measurement of the core body temperature Tcore of the subject O.

According to the present preferred embodiment, one pair of thermal conductive plates 4A and 4B, which sandwich the substrate 2 with the heat receiving terminal 3, and one pair of vias 2A and 2B, which pass through the substrate 2 and which connects the heat receiving terminal 3 to one pair of thermal conductive plates 4A and 4B, respectively, are provided. The first thermal resistance body 10 is provided between the thermal conductive plate 4A and the first input-side temperature sensor 6 and the second thermal resistance body 16 is provided between the thermal conductive plate 4B and the second input-side temperature sensor 12. Accordingly, it is possible to divide the heat (heat flow) received from the subject into the first heat flow Ipa and the second heat flow Ipb with one pair of vias 2A and 2B and one pair of thermal conductive plates 4A and 4B and to supply the first heat flow Ipa and the second heat flow Ipb to the first heat flow measurement system 5 and the second heat flow measurement system 11, respectively. In addition, since the thermal resistance values of the first thermal resistance body 10 and the second thermal resistance body 16 are difficult to vary (are less affected), for example, if the substrate 2 is deformed (for example, is folded), it is possible to stably measure the core body temperature even if the substrate 2 is deformed.

According to the present preferred embodiment, the first input-side heat insulating body 7, which is provided between the first input-side temperature sensor 6 and the first output-side temperature sensor 8 so as to cover the first input-side temperature sensor 6, and the second input-side heat insulating body 13, which is provided between the second input-side temperature sensor 12 and the second output-side temperature sensor 14 so as to cover the second input-side temperature sensor 12, are provided. Accordingly, it is possible to prevent the influence of the air flow to the first input-side temperature sensor 6 and the second input-side temperature sensor 12 and to make the first input-side temperature sensor 6 and the second input-side temperature sensor 12 less affected by the fluctuation of the outside air temperature. Consequently, it is possible to reduce or prevent noise in the outputs from the first input-side temperature sensor 6 and the second input-side temperature sensor 12.

According to the present preferred embodiment, the first output-side heat insulating body 9, which covers the first output-side temperature sensor 8, and the second output-side heat insulating body 15, which covers the second output-side temperature sensor 14, are preferably further provided. Accordingly, it is possible to prevent the influence of the air flow to the first output-side temperature sensor 8 and the second output-side temperature sensor 14 and to make the first output-side temperature sensor 8 and the second output-side temperature sensor 14 less affected by the fluctuation of the outside air temperature. Consequently, it is possible to reduce or prevent noise in the outputs from the first output-side temperature sensor 8 and the second output-side temperature sensor 14.

Figure 4:
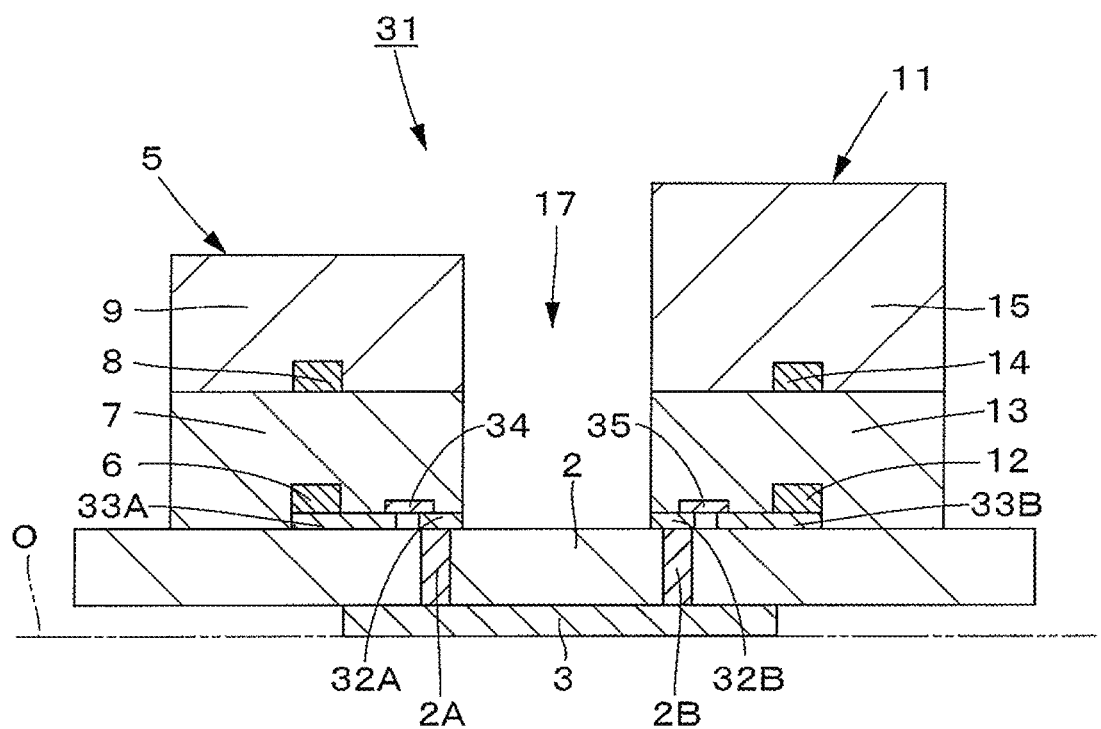
FIG. 4 is a cross-sectional view illustrating the configuration of a core body thermometer according to a second preferred embodiment of the present invention.

A second preferred embodiment of the present invention will now be described with reference to FIG. 4. In the second preferred embodiment, a configuration is provided in which the first and second thermal resistance bodies are provided as first and second thermal resistance components, respectively. The same reference numerals are used in the second preferred embodiment to identify the same components in the first preferred embodiment. A description of such components is omitted herein.

A core body thermometer 31 according to the second preferred embodiment includes the substrate 2, the heat receiving terminal 3, the first heat flow measurement system 5, the second heat flow measurement system 11, input-side thermal conductive plates 32A and 32B, output-side thermal conductive plates 33A and 33B, a first thermal resistance body 34, and a second thermal resistance body 35.

The input-side thermal conductive plate 32A and the output-side thermal conductive plate 33A are positioned on the lower side of the first heat flow measurement system 5 and are provided on the surface of the substrate 2 in a state in which the input-side thermal conductive plate 32A is separated from the output-side thermal conductive plate 33A. The thermal conductive plates 32A and 33A each preferably have a flat plate shape or a film shape that are made of a material, such as aluminum, for example, having a high thermal conductivity, similar to the heat receiving terminal 3. The input-side thermal conductive plate 32A is located at a position closer to the gap 17, which is at a central portion of the substrate 2. The input-side thermal conductive plate 32A is connected to the via 2A. The first input-side temperature sensor 6 in the first heat flow measurement system 5 is provided on the output-side thermal conductive plate 33A. The input-side thermal conductive plate 32A is thermally connected to the output-side thermal conductive plate 33A with the first thermal resistance body 34. Accordingly, the input-side thermal conductive plate 32A and the output-side thermal conductive plate 33A conduct the first heat flow Ipa divided by the heat receiving terminal 3 to the first input-side temperature sensor 6.

The input-side thermal conductive plate 32B and the output-side thermal conductive plate 33B are positioned on the lower side of the second heat flow measurement system 11 and are provided on the surface of the substrate 2 in a state in which the input-side thermal conductive plate 32B is separated from the output-side thermal conductive plate 33B. The thermal conductive plates 32B and 33B each preferably have a flat plate shape or a film shape and are made of a material, such as aluminum, for example, having a high thermal conductivity, similar to the heat receiving terminal 3. The input-side thermal conductive plate 32B is located at a position closer to the gap 17, which is at the central portion of the substrate 2. The input-side thermal conductive plate 32B is connected to the via 2B. The second input-side temperature sensor 12 in the second heat flow measurement system 11 is provided on the output-side thermal conductive plate 33B. The input-side thermal conductive plate 32B is thermally connected to the output-side thermal conductive plate 33B with the second thermal resistance body 35. Accordingly, the input-side thermal conductive plate 32B and the output-side thermal conductive plate 33B conduct the second heat flow Ipb divided by the heat receiving terminal 3 to the second input-side temperature sensor 12.

The first thermal resistance body 34 is a first thermal resistance component provided between the heat receiving terminal 3 and the first input-side temperature sensor 6. Specifically, the first thermal resistance body 34 is provided between the input-side thermal conductive plate 32A, which is connected to the heat receiving terminal 3 with the thermal conductivity, and the output-side thermal conductive plate 33A, which is separated and spaced from the input-side thermal conductive plate 32A. The first thermal resistance body 34 preferably has a chip shape and is made of a material, such as urethane, for example, having a low thermal conductivity and has the predetermined thermal resistance value Ra.

The thermal resistance value Ra of the first thermal resistance body 34 is set in consideration of the thermal isolation between the first heat flow measurement system 5 and the second heat flow measurement system 11. Accordingly, the first thermal resistance body 34 prevents the heat flow from flowing between the first heat flow measurement system 5 and the second heat flow measurement system 11 with the second thermal resistance body 35. The thermal conductivity of the first thermal resistance body 34 is preferably higher than those of the substrate 2 and the first input-side heat insulating body 7. With this configuration, the first heat flow Ipa supplied from the heat receiving terminal 3 to the input-side thermal conductive plate 32A passes through the first thermal resistance body 34, rather than the first input-side heat insulating body 7, and is supplied to the first input-side temperature sensor 6 through the output-side thermal conductive plate 33A.

The second thermal resistance body 35 is a second thermal resistance component provided between the heat receiving terminal 3 and the second input-side temperature sensor 12. Specifically, the second thermal resistance body 35 is provided between the input-side thermal conductive plate 32B, which is connected to the heat receiving terminal 3 with the thermal conductivity, and the output-side thermal conductive plate 33B, which is separated and spaced from the input-side thermal conductive plate 32B. The second thermal resistance body 35 preferably has a chip shape and is made of a material, such as urethane, for example, having a low thermal conductivity and has the predetermined thermal resistance value Rb.

The thermal resistance value Rb of the second thermal resistance body 35 is set in consideration of the thermal isolation between the first heat flow measurement system 5 and the second heat flow measurement system 11. Accordingly, the second thermal resistance body 35 prevents the heat flow from flowing between the first heat flow measurement system 5 and the second heat flow measurement system 11 with the first thermal resistance body 34. The thermal conductivity of the second thermal resistance body 35 is preferably higher than those of the substrate 2 and the second input-side heat insulating body 13.

The sum (Ra+Rb) of the thermal resistances of the first thermal resistance body 34 and the second thermal resistance body 35 is preferably greater than the thermal resistance value Rab between the first input-side temperature sensor 6 and the second input-side temperature sensor 12 (Rab<Ra+Rb), as in the first preferred embodiment.

The sum (Ra+R1+R2) of the thermal resistances of the first thermal resistance body 34, the first input-side heat insulating body 7, and the first output-side heat insulating body 9 is preferably set so as to be different from the sum (Rb+R3+R4) of the thermal resistances of the second thermal resistance body 35, the second input-side heat insulating body 13, and the second output-side heat insulating body 15. As a result, the first heat flow Ipa has a value different from that of the second heat flow Ipb.

As described above, the same or substantially the same effects and advantages as those of the first preferred embodiment are achieved in the second preferred embodiment. According to the core body thermometer 31 of the second preferred embodiment, the first and thermal resistance bodies 34 and 35 are provided as the first and second thermal resistance components having chip shapes. Accordingly, since the profiles of the first and second thermal resistance bodies 34 and 35 is reduced, compared to the core body thermometer in which the first and second thermal resistance bodies are laminated, it is possible to reduce the size of the entire core body thermometer 31.

A third preferred embodiment of the present invention will now be described with reference to FIG. 5 to FIG. 8. A configuration is provided in the third preferred embodiment in which a core body thermometer includes a charging circuit that charges the core body thermometer with electric power that is externally supplied in a wireless manner and a transmission circuit that externally transmits the measured core body temperature. The same reference numerals are used in the third preferred embodiment to identify the same components in the first and second preferred embodiments. A description of such components is omitted herein.

Figure 5:
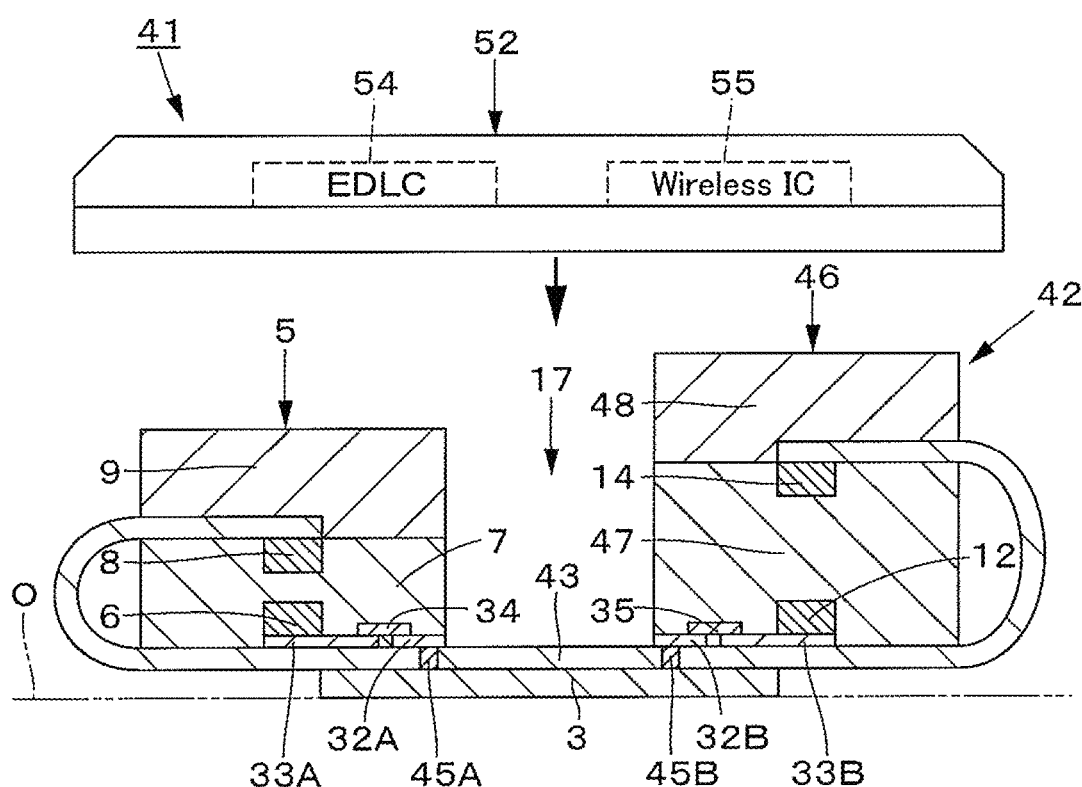
FIG. 5 is a cross-sectional view illustrating the configuration of a core body thermometer according to a third preferred embodiment of the present invention.
Figure 6:
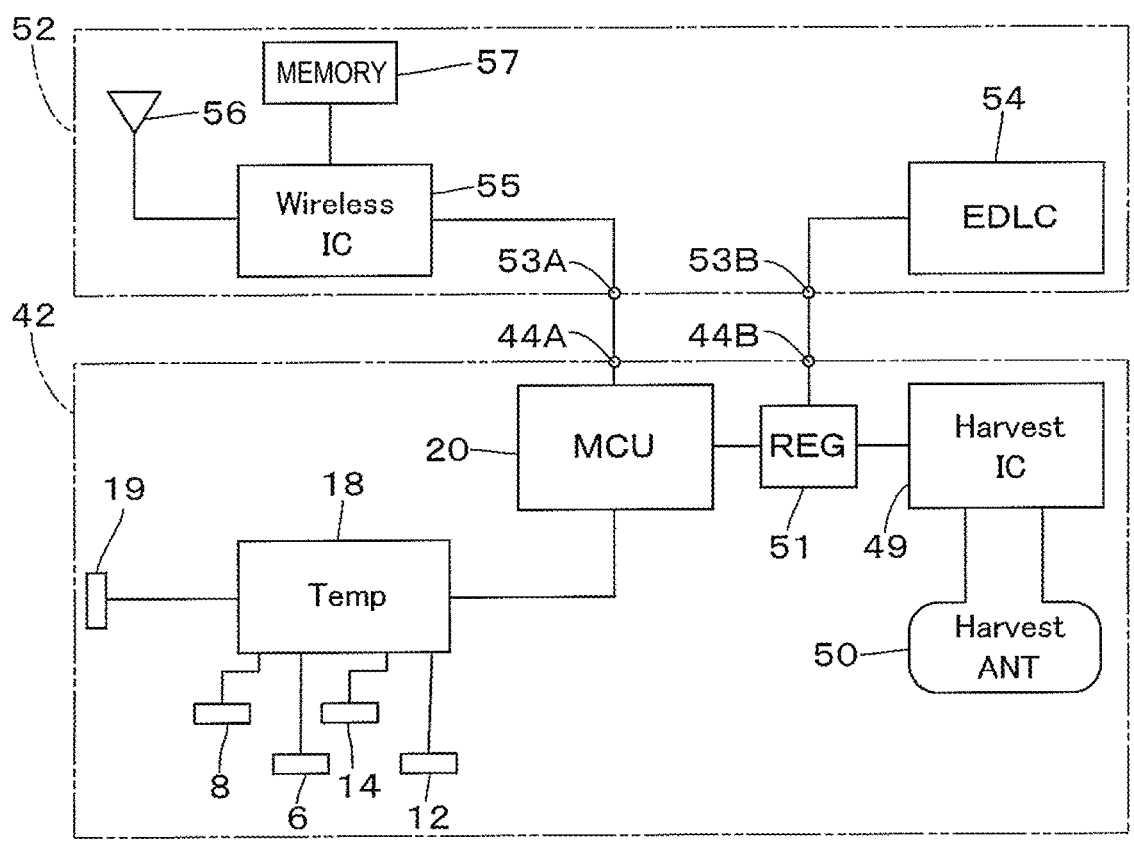
FIG. 6 is a block diagram illustrating the internal configuration of the core body thermometer according to the third preferred embodiment of the present invention.

A core body thermometer 41 according to the third preferred embodiment includes a disposable film portion 42 (a disposable portion) and a repeatedly usable main body 52 (a repeatedly usable portion), as illustrated in FIG. 5 and FIG. 6. The film portion 42 includes a substrate 43, the heat receiving terminal 3, the first heat flow measurement system 5, a second heat flow measurement system 46, the input-side thermal conductive plates 32A and 32B, the output-side thermal conductive plates 33A and 33B, the first thermal resistance body 34, and the second thermal resistance body 35.

The substrate 43 is preferably made of an insulating material, such as polyimide, for example, which has a thermal conductivity lower than that of the subject O. In this case, the substrate 43 is preferably made of, for example, a deformable flexible substrate. The substrate 43 includes a heat receiving portion 43A that is in contact with the subject O and receives heat from the subject O, a first arm portion 43B that extends from the heat receiving portion 43A towards the outside, a second arm portion 43C, a connection terminal portion 43D, and an antenna portion 43E. The first output-side temperature sensor 8 is provided on the first arm portion 43B. The second output-side temperature sensor 14 is provided on the second arm portion 43C. Substrate-side connection terminals 44A and 44B for electrical connection to the main body 52 are provided on the connection terminal portion 43D. The substrate-side connection terminal 44A is connected to the arithmetic processing circuit 20 and the substrate-side connection terminal 44B is connected to a voltage stabilizing circuit 51. A harvesting antenna 50 described below is provided on the antenna portion 43E.

Vias 45A and 45B passing through the substrate 43 in the thickness direction are provided in the substrate 43. The heat receiving terminal 3 is connected to the input-side thermal conductive plate 32A through the via 45A and is connected to the input-side thermal conductive plate 32B through the via 45B.

Figure 7:
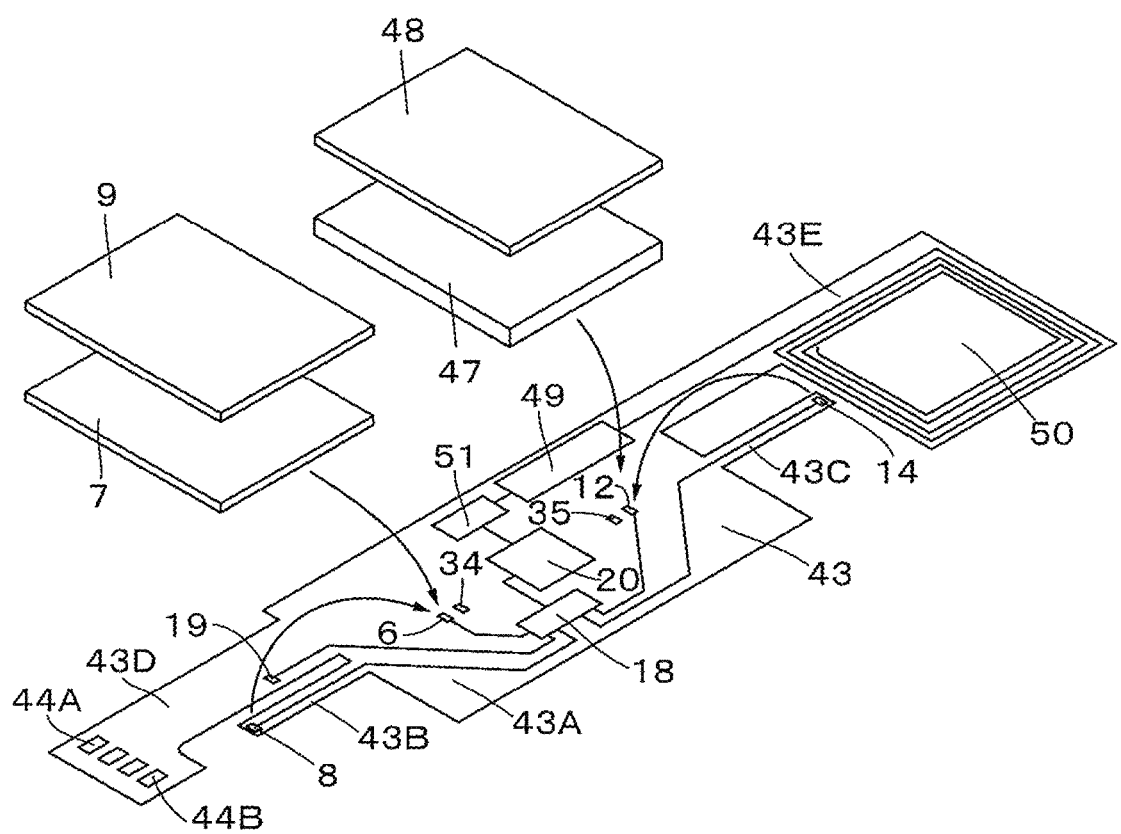
FIG. 7 is a perspective view illustrating a process of providing heat insulating bodies on a substrate of the core body thermometer according to the third preferred embodiment of the present invention.

The front surface (upper surface) of the substrate 43 is a mounting surface on which the input-side thermal conductive plates 32A and 32B, the output-side thermal conductive plates 33A and 33B, the first thermal resistance body 34, the second thermal resistance body 35, the temperature measurement circuit 18, the arithmetic processing circuit 20, a harvesting integrated circuit (IC) 49, the harvesting antenna 50, the voltage stabilizing circuit 51, and other components are mounted, as illustrated in FIG. 5 and FIG. 7.

The second heat flow measurement system 46 is positioned on the upper side of the output-side thermal conductive plate 33B and is provided on the substrate 43. The second heat flow measurement system 46 includes the second input-side temperature sensor 12, a second input-side heat insulating body 47, the second output-side temperature sensor 14, and a second output-side heat insulating body 48. The second heat flow measurement system 46 measures the second heat flow Ipb flowing from the output-side thermal conductive plate 33B to the upper side of the second heat flow measurement system 46 based on the temperatures T3 and T4 measured by the second input-side temperature sensor 12 and the second output-side temperature sensor 14, respectively.

The second input-side heat insulating body 47 is positioned on the surface of the substrate 43 to cover the second input-side temperature sensor 12. The second input-side heat insulating body 47 preferably has a sheet shape and is made of a material, such as urethane, for example, having a low thermal conductivity. The second input-side temperature sensor 12 is sandwiched between the second input-side heat insulating body 47 and the substrate 43.

The second input-side heat insulating body 47 has a predetermined thickness dimension. Accordingly, the second input-side heat insulating body 47 has the predetermined thermal resistance value R3 between the second input-side temperature sensor 12 and the second output-side temperature sensor 14 depending on the thickness dimension. In this case, the second input-side heat insulating body 47 preferably has a thickness dimension greater than that of the first input-side heat insulating body 7 in order to differentiate the heat flow value of the first heat flow Ipa from the heat flow value of the second heat flow Ipb. Accordingly, the thermal resistance value R3 of the second input-side heat insulating body 47 is higher than the thermal resistance value R1 of the first input-side heat insulating body 7.

The second output-side heat insulating body 48 is positioned on the second input-side heat insulating body 47 to cover the second output-side temperature sensor 14. The second output-side heat insulating body 48 preferably has a sheet shape and is made of a material, such as urethane, for example, having a low thermal conductivity. The second output-side temperature sensor 14 is sandwiched between the second output-side heat insulating body 48 and the second input-side heat insulating body 47.

The second output-side heat insulating body 48 is sandwiched between the second output-side temperature sensor 14 and the outside air. The second output-side heat insulating body 48 has a predetermined thickness dimension. Accordingly, the second output-side heat insulating body 48 has the predetermined thermal resistance value R4 between the second output-side temperature sensor 14 and the outside air depending on the thickness dimension. In order to reduce or prevent the influence of the thermal contact resistance, for example, the second output-side heat insulating body 48 and the second input-side heat insulating body 47 preferably have the same or substantially the same thermal conductivity.

The sum (Ra+R1+R2) of the thermal resistances of the first thermal resistance body 34, the first input-side heat insulating body 7, and the first output-side heat insulating body 9 is preferably set so as to be different from the sum (Rb+R3+R4) of the thermal resistances of the second thermal resistance body 35, the second input-side heat insulating body 47, and the second output-side heat insulating body 48, as in the first preferred embodiment described above. As a result, the first heat flow Ipa has a value different from that of the second heat flow Ipb.

The harvesting IC 49 is provided on the substrate 43 and is connected to a battery 54 and the arithmetic processing circuit 20 via the voltage stabilizing circuit 51 described below. The harvesting IC 49 defines and functions as, for example, the charging circuit. The harvesting IC 49 receives radio waves externally transmitted in a wireless manner with the harvesting antenna 50, converts the radio waves into electric power, and charges the battery 54 with the electric power. The harvesting IC 49 may have a configuration in which the core body temperature Tcore of the subject O, calculated by the arithmetic processing circuit 20, is externally transmitted using the harvesting antenna 50.

The voltage stabilizing circuit 51 is provided on the substrate 43 and is connected between the harvesting IC 49 and the arithmetic processing circuit 20. The voltage stabilizing circuit 51 maintains the voltage of a power signal from the harvesting IC 49 at a constant value and supplies the power signal to the battery 54.

The main body 52 preferably has, for example, a rectangular or substantially rectangular parallelepiped shape or a box shape having stiffness with a thickness, as illustrated in FIG. 5 and FIG. 6. The main body 52 includes the battery 54, a wireless IC 55, a transmission antenna 56, a memory 57, and other components. The main body 52 includes a main-body-side connection terminal 53A to be connected to the substrate-side connection terminal 44A and a main-body-side connection terminal 53B to be connected to the substrate-side connection terminal 44B in order to communicate with the arithmetic processing circuit 20 and the harvesting IC 49 at the substrate 43 side (refer to FIG. 6). The main body 52 defines a repeatedly usable module, unlike the substrate 43, which is a disposable portion.

The battery 54 is positioned in the main body 52 and is preferably defined by, for example, an electric double layer capacitor. The battery 54 is connected to the voltage stabilizing circuit 51 via the main-body-side connection terminal 53B and the substrate-side connection terminal 44B. Electric power is supplied from the harvesting IC 49 to the battery 54 and the battery 54 supplies the stored electric power to the arithmetic processing circuit 20 and other components. The battery 54 may not be an electric double layer capacitor and, for example, may have a configuration using a secondary battery.

The wireless IC 55 is positioned in the main body 52 and is preferably defined by, for example, a wireless communication standard using Bluetooth (registered trademark). The wireless IC 55 is connected to the arithmetic processing circuit 20 via the main-body-side connection terminal 53A and the substrate-side connection terminal 44A. The wireless IC 55 defines and functions as the transmission circuit, which transmits the core body temperature Tcore of the subject O, calculated by the arithmetic processing circuit 20 using the first heat flow measurement system 5 and the second heat flow measurement system 46, to an external device via the transmission antenna 56. In this case, the wireless IC 55 may store the calculated core body temperature Tcore in the memory 57.

A process of assembling the core body thermometer 41 will now be described with reference to FIG. 7 and FIG. 8.

First, as illustrated in FIG. 7, the respective temperature sensors 6, 8, 12, and 14, the temperature measurement circuit 18, the arithmetic processing circuit 20, the harvesting IC 49, the harvesting antenna 50, the voltage stabilizing circuit 51, and other components are mounted on the substrate 43. Then, the first input-side heat insulating body 7 is fixed on the first input-side temperature sensor 6 and the second input-side heat insulating body 47 is fixed on the second input-side temperature sensor 12.

Figure 8:
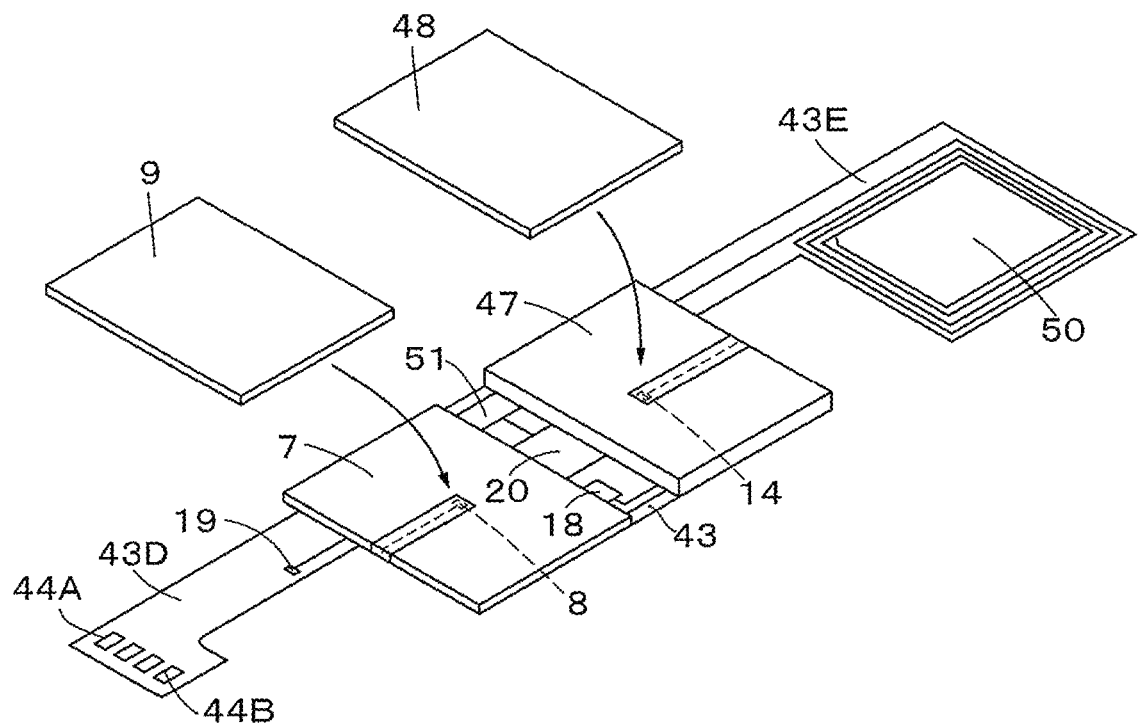
FIG. 8 is a perspective view illustrating a process of providing the heat insulating bodies on the respective output-side temperature sensors, following the process in FIG. 7.

Next, as illustrated in FIG. 8, the first arm portion 43B of the substrate 43 is folded back toward the heat receiving portion 43A side to place the first output-side temperature sensor 8 on the first input-side heat insulating body 7. Similarly, the second arm portion 43C of the substrate 43 is folded back toward the heat receiving portion 43A side to place the second output-side temperature sensor 14 on the second input-side heat insulating body 47. Then, the first output-side heat insulating body 9 is fixed on the first output-side temperature sensor 8 and the second output-side heat insulating body 48 is fixed on the second output-side temperature sensor 14.

Here, the first heat flow measurement system 5 is spaced away from the second heat flow measurement system 46 to provide the gap 17 between the first heat flow measurement system 5 and the second heat flow measurement system 46. Finally, the main body 52 is placed on the first output-side heat insulating body 9 and the second output-side heat insulating body 48 and the substrate-side connection terminals 44A and 44B are connected to the main-body-side connection terminals 53A and 53B, respectively, to complete the core body thermometer 41.

As described above, substantially the same effects and advantages as those of the first preferred embodiment are achieved in the third preferred embodiment. According to the third preferred embodiment, the core body thermometer 41 has a configuration including the harvesting IC 49 capable of being charged with the radio waves externally transmitted in a wireless manner and the wireless IC 55 capable of externally transmitting the core body temperature Tcore of the subject O. Accordingly, since the core body thermometer 41 is capable of being used with no cable and the wiring is not used in the measurement of the core body temperature Tcore, it is possible to improve non-invasiveness.

In the configuration in the third preferred embodiment, the first thermal resistance component is preferably used as the first thermal resistance body 34 and the second thermal resistance component is used as the second thermal resistance body 35, as in the second preferred embodiment. However, the present invention is not limited to this configuration and the configuration may be provided, as in the first preferred embodiment, in which the first thermal resistance layer is provided between the substrate and the first input-side heat insulating body as the first thermal resistance body and the second thermal resistance layer is provided between the substrate and the second input-side heat insulating body as the second thermal resistance body.

Figure 9:
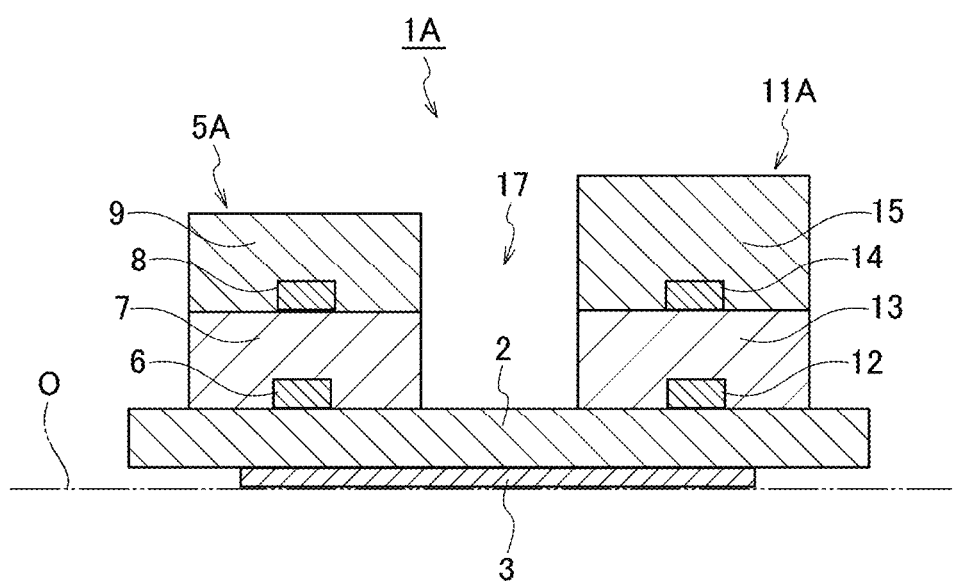
FIG. 9 is a cross-sectional view illustrating the configuration of a core body thermometer according to a fourth preferred embodiment of the present invention.

A core body thermometer 1A according to a fourth preferred embodiment of the present invention will now be described with reference to FIG. 9. A description of the same components as those in the first preferred embodiment described above and the components similar to those in the first preferred embodiment described above is simplified or omitted herein and only different points will be primarily described. FIG. 9 is a cross-sectional view illustrating the configuration of the core body thermometer 1A according to the fourth preferred embodiment. The same reference numerals are used in FIG. 9 to identify the same components as those in the first preferred embodiment described above and the components similar to those in the first preferred embodiment described above.

The core body thermometer 1A differs from the core body thermometer 1 according to the first preferred embodiment described above in that the core body thermometer 1A includes a first heat flow measurement system 5A, instead of the first heat flow measurement system 5, and a second heat flow measurement system 11A, instead of the second heat flow measurement system 11. The first heat flow measurement system 5A differs from the first heat flow measurement system 5 described above in that the first heat flow measurement system 5A does not include the via 2A and the thermal conductive plate 4A and a substrate 2 having the predetermined thermal resistance value Rc has the function of the first thermal resistance body 10, instead of the first thermal resistance body 10 having the predetermined thermal resistance value Ra. The second heat flow measurement system 11A differs from the second heat flow measurement system 11 described above in that the second heat flow measurement system 11A does not include the via 2B and the thermal conductive plate 4B and the substrate 2 having the predetermined thermal resistance value Rc has the function of the second thermal resistance body 16, instead of the second thermal resistance body 16 having the thermal resistance value Rb.

The first heat flow measurement system 5A is positioned on the upper side of the substrate 2. The first heat flow measurement system 5A includes the first input-side temperature sensor 6, the first input-side heat insulating body 7, the first output-side temperature sensor 8, and the first output-side heat insulating body 9. In the first heat flow measurement system 5A, the first input-side temperature sensor 6 and the first output-side temperature sensor 8 are located at different positions along a path on which the first heat flow Ipa, which is divided and flows into the core body thermometer 1A via the heat receiving terminal 3 and the substrate 2, flows. With the above configuration, the first heat flow measurement system 5A measures the first heat flow Ipa flowing from the substrate 2 to the upper side of the first heat flow measurement system 5A based on the temperatures T1 and T2 measured by the first input-side temperature sensor 6 and the first output-side temperature sensor 8, respectively.

The second heat flow measurement system 11A is provided on the upper side of the substrate 2. The second heat flow measurement system 11A includes the second input-side temperature sensor 12, the second input-side heat insulating body 13, the second output-side temperature sensor 14, and the second output-side heat insulating body 15. In the second heat flow measurement system 11A, the second input-side temperature sensor 12 and the second output-side temperature sensor 14 are located at different positions on a path on which the second heat flow Ipb, which is divided and flows into the core body thermometer 1A via the heat receiving terminal 3 and the substrate 2, flows. With the above configuration, the second heat flow measurement system 11A measures the second heat flow Ipb flowing from the thermal conductive plate 2A to the upper side of the second heat flow measurement system 11A based on the temperatures T3 and T4 measured by the second input-side temperature sensor 12 and the second output-side temperature sensor 14, respectively.

The sum (Rc+R1+R2) of the thermal resistances of the substrate 2, the first input-side heat insulating body 7, and the first output-side heat insulating body 9 is preferably set so as to be different from the sum (Rc+R3+R4) of the thermal resistances of the substrate 2, the second input-side heat insulating body 13, and the second output-side heat insulating body 15. As a result, the first heat flow Ipa has a value different from that of the second heat flow Ipb. Since the remaining configuration is the same as or similar to that of the first preferred embodiment described above, a detailed description of the remaining configuration is omitted herein.

According to the present preferred embodiment, the core body temperature is capable of being estimated with the heat from the subject O being input into the core body thermometer 1A at one node with no heat source for heat generation, as in the first preferred embodiment described above. In particular, according to the present preferred embodiment, the substrate 2 preferably has the predetermined thermal resistance value Rc and the substrate 2 is able to be used as the first thermal resistance body 10 and the second thermal resistance body 16 described above. In other words, the substrate 2 preferably also has the functions of the first thermal resistance body 10 and the second thermal resistance body 16. Accordingly, it is possible to further simplify the structure of the core body thermometer 1A to reduce the size and the weight (make the profile low) and to reduce the cost.

Figure 10:
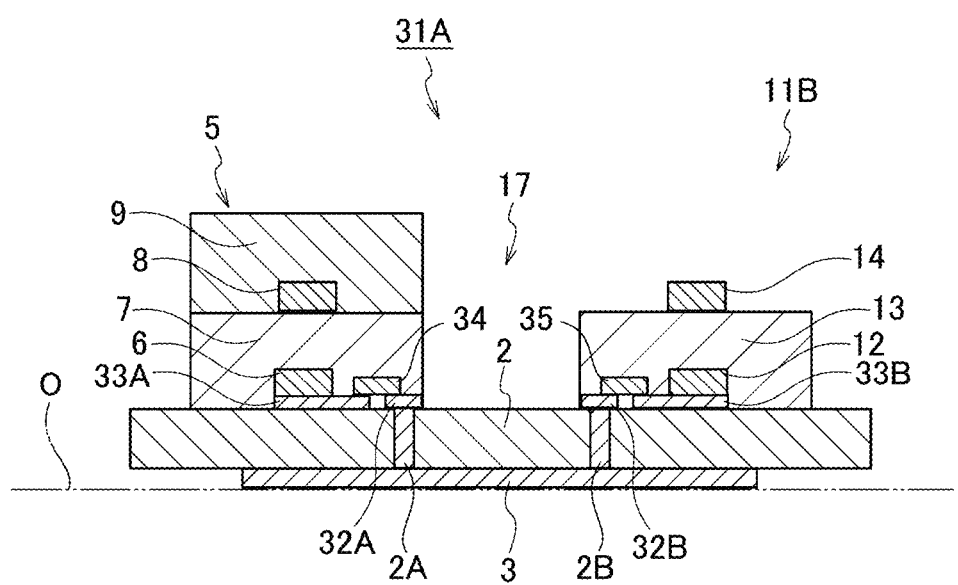
FIG. 10 is a cross-sectional view illustrating the configuration of a core body thermometer according to a fifth preferred embodiment of the present invention.

A core body thermometer 31A according to a fifth preferred embodiment of the present invention will now be described with reference to FIG. 10. FIG. 10 is a cross-sectional view illustrating the configuration of the core body thermometer 31A according to the fifth preferred embodiment. The same reference numerals are used in FIG. 10 to identify the same components as those in the second preferred embodiment described above and the components similar to those in the second preferred embodiment described above.

The core body thermometer 31A differs from the core body thermometer 31 according to the second preferred embodiment described above in that the core body thermometer 31A includes a second heat flow measurement system 11B, instead of the second heat flow measurement system 11. The second heat flow measurement system 11B differs from the second heat flow measurement system 11 described above in that the second heat flow measurement system 11B does not include the second output-side heat insulating body 15.

The second heat flow measurement system 11B is provided on the upper side of the thermal conductive plate 33B. The second heat flow measurement system 11B includes the second input-side temperature sensor 12, the second input-side heat insulating body 13, and the second output-side temperature sensor 14. In the second heat flow measurement system 11B, the second input-side temperature sensor 12 and the second output-side temperature sensor 14 are located at different positions along a path on which the second heat flow Ipb flows. With this configuration, the second heat flow measurement system 11B measures the second heat flow Ipb flowing from the thermal conductive plate 33B to the upper side of the second heat flow measurement system 11B based on the temperatures T3 and T4 measured by the second input-side temperature sensor 12 and the second output-side temperature sensor 14, respectively.

The sum (Ra+R1+R2) of the thermal resistances of the first thermal resistance body 34, the first input-side heat insulating body 7, and the first output-side heat insulating body 9 is preferably set so as to be different from the sum (Rb+R3) of the thermal resistances of the second thermal resistance body 35 and the second input-side heat insulating body 13. As a result, the first heat flow Ipa has a value different from that of the second heat flow Ipb. Since the remaining configuration is the same as or similar to that of the second preferred embodiment described above, a detailed description of the remaining configuration is omitted herein.

According to the present preferred embodiment, the core body temperature is capable of being estimated with the heat from the subject O being input into the core body thermometer 31A at one node with no heat source for heat generation, as in the second preferred embodiment described above. In particular, according to the present preferred embodiment, omitting the second output-side heat insulating body 15 enables the configuration of the core body thermometer 31A to be further simplified to reduce the size and the weight (make the profile low) and to reduce the cost.

Although the preferred embodiments of the present invention have been described, the present invention is not limited to the preferred embodiments and various modifications may be made. For example, a configuration may be provided in which either of the first output-side heat insulating body 9 and the second output-side heat insulating body 15 of the core body thermometer 1A according to the fourth preferred embodiment is not provided or both of the first output-side heat insulating body 9 and the second output-side heat insulating body 15 are not provided. In addition, a configuration may be provided in which a combination of the first heat flow measurement system 5A and the second heat flow measurement system 11A of the core body thermometer 1A according to the fourth preferred embodiment with the first heat flow measurement system 5 and the second heat flow measurement system 11 of the core body thermometer 1 according to the first preferred embodiment is used.

Although the configuration is provided in which the first output-side heat insulating body 9 is provided and the second output-side heat insulating body 15 is not provided in the fifth preferred embodiment described above, a configuration may be provided in which the second output-side heat insulating body 15 is provided and the first output-side heat insulating body 9 is not provided. Alternatively, a configuration may be provided in which both of the first output-side heat insulating body 9 and the second output-side heat insulating body 15 are not provided.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A core body thermometer that estimates a core body temperature of a subject based on a first heat flow and a second heat flow flowing from the subject, the core body thermometer comprising:
    a substrate;
    a heat receiving terminal provided on or in the substrate, with which heat from the subject is received, and which is configured to divide the heat into the first heat flow and the second heat flow;
    a first heat flow measurement system that is configured to measure the first heat flow using a first input-side temperature sensor located at an upstream side of the first heat flow and a first output-side temperature sensor located at a downstream side of the first heat flow;
    a second heat flow measurement system that is configured to measure the second heat flow using a second input-side temperature sensor located at an upstream side of the second heat flow and a second output-side temperature sensor located at a downstream side of the second heat flow;
    a first thermal resistance body provided between the heat receiving terminal and the first input-side temperature sensor and having a predetermined thermal resistance value; and
    a second thermal resistance body provided between the heat receiving terminal and the second input-side temperature sensor and having a predetermined thermal resistance value.

2. The core body thermometer according to claim 1, wherein
    the first thermal resistance body is a first thermal resistance layer located between the heat receiving terminal and the first input-side temperature sensor; and
    the second thermal resistance body is a second thermal resistance layer located between the heat receiving terminal and the second input-side temperature sensor.

3. The core body thermometer according to claim 1, wherein
    the first thermal resistance body is a first thermal resistance component; and
    the second thermal resistance body is a second thermal resistance component.

4. The core body thermometer according to claim 1, further comprising:
    one pair of thermal conductive plates sandwiching the substrate with the heat receiving terminal; and
    a plurality of vias passing through the substrate and connecting the heat receiving terminal to the one pair of thermal conductive plates; wherein
    the first thermal resistance body is provided between one of the pair thermal conductive plates and the first input-side temperature sensor; and
    the second thermal resistance body is provided between another of the pair of thermal conductive plates and the second input-side temperature sensor.

5. The core body thermometer according to claim 1, further comprising:
    a first input-side heat insulating body disposed between the first input-side temperature sensor and the first output-side temperature sensor so as to cover the first input-side temperature sensor; and
    a second input-side heat insulating body disposed between the second input-side temperature sensor and the second output-side temperature sensor so as to cover the second input-side temperature sensor.

6. The core body thermometer according to claim 5, further comprising a first output-side heat insulating body that covers the first output-side temperature sensor and/or a second output-side heat insulating body that covers the second output-side temperature sensor.

7. The core body thermometer according to claim 1, further comprising:
    a charging circuit that is configured to charge the core body thermometer with electric power that is externally supplied in a wireless manner; and
    a transmission circuit that is configured to externally transmit the core body temperature of the substrate, which is estimated with the first heat flow measurement system and the second heat flow measurement system.

8. The core body thermometer according to claim 1, wherein the substrate has a flat plate shape and is made of an insulating material.

9. The core body thermometer according to claim 1, wherein the substrate is made of polyimide.

10. The core body thermometer according to claim 1, wherein the substrate has a thermal conductivity lower than that of the subject.

11. The core body thermometer according to claim 1, wherein the heat receiving terminal has a flat plate shape or a film shape.

12. The core body thermometer according to claim 1, wherein the heat receiving terminal is made of a material having a thermal conductivity higher than that of the subject.

13. The core body thermometer according to claim 1, wherein the heat receiving terminal is made of aluminum.

* * * * *